United States Patent [19]
Hall

[11] 4,041,939
[45] Aug. 16, 1977

[54] SURGICAL IMPLANT SPINAL SCREW
[75] Inventor: John Emmett Hall, Boston, Mass.
[73] Assignee: Downs Surgical Limited, Mitcham, England
[21] Appl. No.: 680,234
[22] Filed: Apr. 26, 1976
[30] Foreign Application Priority Data
    Apr. 28, 1975  United Kingdom .............. 17612/75
[51] Int. Cl.² .......................... A61F 5/00; A61B 17/18
[52] U.S. Cl. .................................... 128/69; 128/92 B;
                                          128/78; 85/9 R; 85/46
[58] Field of Search ................ 128/92 B, 92 R, 92 A,
    128/92 BB, 92 BC, 92 D, 67, 78; 46/9 R, 46;
                                                            151/16

[56]            References Cited
         U.S. PATENT DOCUMENTS
    1,028,795   6/1912   Steinhouse ............................. 85/46
    2,532,296  12/1950   Giesen ................................. 128/92 B OTHER PUBLICATIONS
"Self-Broaching Hansen-Street Nail", DePuy Catalog, Depuy Inc., Warsaw, Ind. p. 32, Copyright 1969, received Scientific Library, Mar. 28, 1975.
"A New Surgical Approach for Correcting the Scoliotic Spine Using a Tensioned Cable Secured to the Convex Curve of the Affected Vertebrae" by A. F. Dwyer, Advertisement p. 57, The Journal of Bone & Joint Surgery, vol. 53A, No. 2, Mar. 1971.

Primary Examiner—Ronald L. Frinks
Attorney, Agent, or Firm—Haight & Huard, Chartered

[57]              ABSTRACT
Surgical implant, known as a spinal screw and nut, for use in securing a metal cable to a vertebrae in an operation for the correction of scoliosis.

10 Claims, 3 Drawing Figures

SURGICAL IMPLANT SPINAL SCREW

This invention relates to a surgical implant for use in the correction of curvature of the spinal column.

One technique that is used for the correction of the spinal curvatures is the Dwyer technique of anterior instrumentation of the spine; (c.f. A.F. Dwyer, "Anterior approach to scoliosis", *Journal of the Western Pacific Orthopaedic Association, Vol. VI,* No. 1, March 1969; A.F. Dwyer et al, "Anterior approach to scoliosis", *Clinical Orthopaedics and Related Research,* No. 62, pp. 192–202, 1969; and A.F. Dwyer, "Anterior approach to scoliosis", ibid, No. 93, July 1973). This technique involves operation on the front of the spine, with access to the spine being gained by the removal of one rib, or possibly of two ribs. This method may be used for the correction of scoliosis (lateral curvature of the spinal column) when posterior elements are absent, such as in myelomeningocele or after an extensive laminectomy. It is particularly useful when lordosis (curvature of the spinal column with a forward convexity) is associated with scoliosis, and can often be used as a supplementary means of fixation in very long paralytic curves, especially those associated with lordosis in the lumbar region.

The technique involves the application of compression on the convex side of the spinal curve, after the contents of the discs have been excised, so as to straighten the curve. The compression is applied by means of a metal cable threaded through the heads of screws, one of which is anchored through a metal staple in each vertebra.

A staple of "saddle" of such a size as to fit snugly over the vertebra is first selected and driven into place over the vertebra. A screw is then passed through a hole in the staple and into the vertebra until only the head of the screw protrudes above the staple. A metal cable is passed through a hole in the head of the screw. The procedure is repeated on successive vertebrae with a single cable being passed through all screw heads. Tension is applied to the cable, to obtain the necessary corrective force, by means of a special tensioner. The tension may be applied one stage at a time, after the cable has been passed through each respective screw-head, or it may be applied after the cable has been passed through several or all of the screw-heads. When the correct tension has been obtained, the screw-head is crimped over the cable so as to maintain the cable at the necessary tension.

The screws that have been used for securing the cable to the vertebrae have been self-tapping screws having a buttress thread and with an eyelet in the screw-head to receive the metal cable. The length of screw chosen for any particular application is generally such that the point of the screw will almost or will just penetrate the back of the respective vertebra, the screw being introduced from the front of the vertebra. For most purposes, the screw is held sufficiently firmly in place simply by being screwed into the vertebra. There are occassions, however, when the screw cannot be secured sufficiently firmly solely by being screwed into the vertebra. This is particularly so in the case of the first, generally the top, screw to be applied. In this case the tension subsequently applied to the cable threaded through the screw-head can cause a loosening or dislodgement of the screw in the vertebra, which is obviously to be avoided.

The present invention provides a surgical implant which comprises a combination of a metal spinal screw and a metal nut, wherein the screw has a head provided with a hole through which a metal cable can be passed, the head being capable of being deformed to prevent movement of the cable within the hole, and a shank having a relatively coarse self-tapping thread over a major portion of its length and, on an end portion remote from the head, a relatively fine thread of smaller external diameter, and wherein the nut has an internal thread compatible with the fine-threaded end portion of the shank of the screw, and a plastics insert adjacent to a portion of the internal thread and so arranged that, in use, it can engage a part of the fine-threaded end portion of the screw.

The present invention also provides a screw as defined above.

The head of the screw is provided with a hole to accommodate a metal cable, and has also to be capable of being deformed (or crimped), so as to secure the cable to the screw. In both these respects the head can be similar to that of a conventional spinal screw.

The shank of the screw is threaded, over a major portion of its length, with a relatively coarse self-tapping thread, and this can be similar to the thread used on a conventional spinal screw, for example, a buttress thread. The end portion of the shank remote from the head is threaded with a relatively fine thread of smaller external diameter than that of the coarse thread. It is onto this part of the screw that the nut can be screwed.

The nut has an internal thread compatible with the fine-threaded end portion of the screw. It also has a plastics, preferably nylon, insert adjacent to a portion of the internal thread. This plastics insert causes the nut to have a self-locking action. The part of the insert adjacent to the internal thread is tapped by the fine-threaded end of the screw as the nut is screwed onto this end of the screw. This plastics insert thus grips the thread of the screw sufficiently firmly to prevent the nut from loosening itself. The nut may suitably be hexagonal. Advantageously, the plastics insert penetrates from a face of the nut to the internal thread.

The length of the coarse-threaded portion of the screw is suitably from 20 to 30 mm. It is generally suitable to manufacture screws in various sizes such that the length of the said portion varies in, say 2 mm steps from 20 to 30 mm. In this way, a suitably sized screw can be chosen for any particular application. The length of the fine-threaded end portion of the screw, to accommodate the nut, can be the same for all sizes of screws and is suitably from 5 to 10 mm long.

The screw and nut will generally be made of titanium, since this metal neither adversely affects, nor is adversely affected by, body tissue.

When using the surgical implant according to the invention, a spinal staple is driven into place on the front of the vertebra in the usual manner, and the screw is then screwed, through the hole in the spinal staple, into the vertebra. When the screw has been screwed completely home, with its head abutting the spinal staple, the coarse-threaded self-tapping portion of the shank should be contained wholly within the vertebra, but should penetrate almost to the back of the vertebra, and the fine-threaded end portion of the shank should protrude from the back of the vertebra to an extent at least sufficient to enable the nut to be securely screwed onto the screw and against the back of the vertebra so as to secure the screw in place. The size of screw used for any particular application should be chosen accordingly, with the thickness of the staple being taken into account.

One form of screw and nut according to the invention will now be described, by way of example only, with reference to the accompanying drawings, in which.

Figure 1:
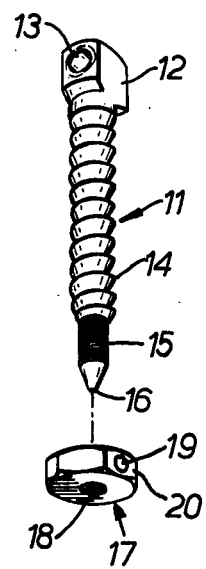
FIG. 1 is a perspective view of the screw and nut.
Figure 2:
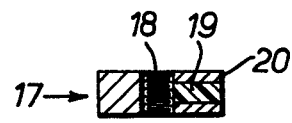
FIG. 2 is a cross-sectional view through the nut.

Referring to FIG. 1, the screw 11 has a head 12 provided with a hole 13 to accommodate a metal cable (not shown). The shank of the screw is, over a major portion of its length, threaded with a coarse self-tapping buttress thread 14. The end portion of the screw remote from the head is of smaller external diameter and is threaded with a somewhat finer thread 15, and the screw terminates in a point 16. The nut 17 is hexagonal, and has an internal thread 18 compatible with the fine thread 15 at the end portion of the screw. A nylon insert 19 penetrates from one face 20 of the nut to the internal thread 18, as can clearly be seen in FIG. 2.

Figure 3:
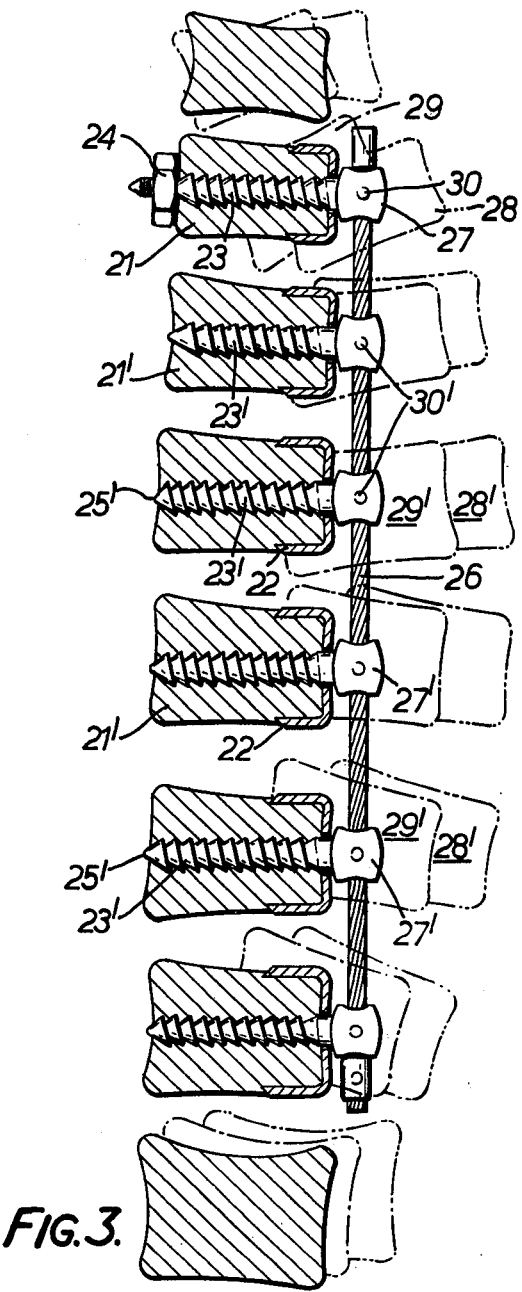
FIG. 3 is a diagrammatic view of a spinal column in which a screw and nut according to the invention have been used on one vertebra.

Referring to FIG. 3, each vertebra 21, 21', has had a spinal staple 22 driven over it, and has had a spinal screw 23, 23' respectively screwed through a hole in the staple and into the vertebra. In the uppermost vertebra 21 to have been instrumented, the spinal screw 23 used is as shown in FIG. 1, and a nut 24 has been screwed onto the fine-threaded end portion of the screw 23 protruding from the vertebra 21. In all the other vertebra 21 that have been instrumented, conventional spinal screws 23', without a fine-threaded end portion, have been used; in these cases the point 25' of each screw 23' just penetrates the back of the respective vertebra 21'. A cable 26 has been threaded through the screw-heads 27, 27', and tension has been applied to straighten the spinal column so that the vertebrae have moved from the positions 28, 28', through the positions 29, 29' respectively, to the positions 21, 21' respectively. When the desired tension had been obtained and the spinal column straightened the screw-heads 27, 27' were crimped at 30, 30' respectively to secure them to the cable 26 and thus maintain the desired tension. The use of a screw 23 and nut 24 according to the invention in the top vertebra 21 prevents the screw from loosening when tension is applied to the cable. There is less danger of such loosening occuring in the other vertebrae 21' and therefore conventional screws 23' can be used here.

Certain further surgical implants for use in the Dwyer technique of anterior instrumentation of the spine are described and claimed in the complete specifications accompanying U.K. patent applications Nos. 17610/75 and 17611/75 respectively. A surgical instrument for use in applying tension to the cable threaded through the screw-heads is described and claimed in the complete specification accompanying U.K. patent application No. 17613/75.

What I claim is:

1. A surgical implant which comprises a combination of a metal spinal screw and a metal nut, wherein the screw has a head provided with a hole through which a metal cable can be passed, the head being capable of being deformed to prevent movement of the cable within the hole, and a shank having a relatively coarse self-tapping thread over a major portion of its length and, on an end portion remote from the head, a relatively fine thread of smaller external diameter, and wherein the nut has an internal thread compatible with the fine-threaded end portion of the shank of the screw, and a plastics insert adjacent to a portion of the internal thread and so arranged that, in use, it can engage a part of the fine-threaded end portion of the screw.

2. A surgical implant which comprises a metal spinal screw having a head provided with a hole through which a metal cable can be passed, the head being capable of being deformed to prevent movement of the cable within the hole, and a shank having a relatively coarse self-tapping thread over a major portion of its length proximate said head and, on an end portion remote from the head, a relatively fine nut-receiving thread of smaller external diameter.

3. An implant as claimed in claim 1, wherein the length of the coarse-threaded portion of the screw is from 20 to 30 mm and the length of the fine-threaded end portion of the screw is from 5 to 10 mm.

4. An implant as claimed in claim 1, wherein the screw is made of titanium.

5. An implant as claimed in claim 1, wherein the plastics insert of the nut is of nylon.

6. An implant as claimed in claim 1, wherein the nut is hexagonal.

7. An implant as claimed in claim 1, wherein the plastics insert penetrates from a face of the nut to the internal thread.

8. An implant as claimed in claim 1, wherein the metal of which the nut is made is titanium.

9. An implant as claimed in claim 2, wherein the length of the coarse-threaded portion of the screw is from 20 to 30 mm and the length of the fine-threaded end portion of the screw is from 5 to 10 mm.

10. An implant as claimed in claim 2, wherein the screw is made of titanium.

* * * * *